US012514737B1

(12) United States Patent
He et al.

(10) Patent No.: US 12,514,737 B1
(45) Date of Patent: Jan. 6, 2026

(54) PENILE PUMP

(71) Applicant: Kechao He, Sichuan (CN)

(72) Inventors: Kechao He, Sichuan (CN); Hanwu Lin, Guangdong (CN)

(*) Notice: Subject to any disclaimer, the term of this patent is extended or adjusted under 35 U.S.C. 154(b) by 0 days.

(21) Appl. No.: 19/215,952

(22) Filed: May 22, 2025

(30) Foreign Application Priority Data

May 7, 2025 (CN) ......................... 202520881446.3

(51) Int. Cl.
*A61F 5/41* (2006.01)

(52) U.S. Cl.
CPC .......... *A61F 5/41* (2013.01); *A61F 2005/412* (2013.01); *A61F 2005/414* (2013.01); *A61F 2005/417* (2013.01)

(58) Field of Classification Search
CPC ................ A61H 23/0263; A61H 19/32; A61H 2023/0281; A61F 5/41; A61F 2005/412; A61F 2005/417
See application file for complete search history.

(56) References Cited

U.S. PATENT DOCUMENTS 11,007,110 B1 * 5/2021 Zhou .................. A61H 23/0263
2002/0169400 A1 * 11/2002 Huang ............... A61H 23/0254
601/134

* cited by examiner

*Primary Examiner* — Samuel G Gilbert

(57) ABSTRACT

A penile pump includes a head cover, a bottom end of the head cover is fixedly connected to a main body; a bottom end of the main body is fixedly connected to a base, a square box is fixedly connected inside the base, inside the square box is fixedly connected with a support frame, both left and right sides of the support frame are fixedly connected to connecting plates, an interior of the connecting plate is rotatably connected to a connecting rod, a bottom end of the connecting rod is fixed with a dual-head motor, and left and right driving ends of the dual-head motor are connected to eccentric wheels; both front and back sides of the eccentric wheel are fixedly connected to first fixing rods. In the invention, vibration helps promote the local metabolism of the penis, allowing cells to obtain more sufficient nutrients and oxygen.

10 Claims, 3 Drawing Sheets

PENILE PUMP

1. TECHNICAL FIELD

The invention belongs to the technical field of treatment of male sexual dysfunction, specifically relates to a penile pump.

2. BACKGROUND ART

A penile pump is a medical device designed to assist men in improving erectile function, also known as a vacuum erection device (VED). It typically consists of a vacuum pump or manual suction mechanism that creates a negative pressure environment around the penis by removing air from a cylinder placed over it. This negative pressure causes the blood vessels in the penile corpus cavernosum to expand, increasing blood flow and leading to penile engorgement and erection. Once a satisfactory erection degree is achieved, a constriction ring is applied to maintain the erection by preventing blood from flowing back out, enabling sexual intercourse.

In addition to promoting blood circulation and activating penile nerves as previously mentioned, the vibration function of the penile pump offers several benefits. Vibration provides a massaging effect that helps relieve tension in the muscles surrounding the penis. It also aids users in relaxing both physically and mentally, reducing anxiety and psychological stress often associated with erectile dysfunction, thereby improving sexual performance to some extent. The additional vibratory stimulation enhances sexual sensation, making it easier for men to reach sexual arousal, which is particularly helpful for those with difficulties in sexual arousal, ultimately enhancing sexual experience and satisfaction. Furthermore, vibration promotes local metabolism in the penis, ensuring cells receive adequate nutrients and oxygen, which is beneficial for maintaining penile tissue health and may have long-term positive effects on erectile function.

While the negative pressure principle of a penile pump inherently facilitates blood flow into the penis, vibration can further accelerate local circulation. Without the vibration function, the device may be less effective in promoting blood flow, requiring longer treatment periods to achieve noticeable results or potentially resulting in less stable erections for individuals with erectile dysfunction caused by poor blood circulation. Vibration also plays a role in relaxing penile muscles and activating nerves; its absence weakens these effects, necessitating alternative methods for muscle relaxation and nerve stimulation, which may hinder recovery for patients with erectile issues related to muscle tension or nerve function. Therefore, we present a penile pump to solve the above problem.

3. SUMMARY OF THE INVENTION

To address these shortcomings, the invention introduces a penile pump, which aims to overcome the limitations of the prior art, such as relatively single stimulation effects, limited muscle relaxation and nerve activation capabilities, and suboptimal blood circulation promotion.

To achieve the above objectives, the invention employs the following technical solutions:

a penile pump includes a head cover, a bottom end of the head cover is fixedly connected to a main body; a bottom end of the main body is fixedly connected to a base, a square box is fixedly connected inside the base, inside the square box is fixedly connected with a support frame, both left and right sides of the support frame are fixedly connected to connecting plates, an interior of the connecting plate is rotatably connected to a connecting rod, a bottom end of the connecting rod is fixed with a dual-head motor, and left and right driving ends of the dual-head motor are connected to eccentric wheels; both front and back sides of the eccentric wheel are fixedly connected to first fixing rods, far sides of the two first fixing rods are both fixedly connected to springs; an adjacent side of the support frame is fixedly connected to second fixing rods; a bottom end of the head cover is sleeved with a sealing component.

As a further elaboration of the above technical solution, the sealing component includes a silicone ring; an outer side of the silicone ring is sleeved inside the main body; an interior of the head cover is fixedly connected to a pressing piece;

As a further elaboration of the above technical solution, a bottom end of the pressing piece is fixedly connected to a fixing piece, inside a front end of the main body is fixedly connected with a flexible PCB;

As a further elaboration of the above technical solution, inside the head cover is fixedly connected with a charging head; inside the front end of the main body, on a right side is fixedly connected with a right button PCB;

As a further elaboration of the above technical solution, on a left side of the front end of the main body is fixedly connected with a left button PCB, a front end of the right button PCB is fixedly connected to a right silicone button;

As a further elaboration of the above technical solution, a front end of the left button PCB is fixedly connected to a left silicone button, a front end of the main body is fixedly connected to a sealing ring;

As a further elaboration of the above technical solution, a front end of the left button PCB is connected to a transparent mask, a front end of the flexible PCB is fixedly connected to a back end of the transparent mask;

As a further elaboration of the above technical solution, inside the fixing piece is fixedly connected with a water pump; a back end of the fixing piece is fixedly connected to a battery;

As a further elaboration of the above technical solution, on a right side of the fixing piece is fixedly connected with an air release valve, on a right side of an interior of the base is fixedly connected with a main PCB;

As a further elaboration of the above technical solution, an outer side of the right silicone button is slidably connected inside the main body, an outer side of the left silicone button is slidably connected inside the main body; an interior of the sealing ring is sleeved at the front end of the flexible PCB.

The invention has the following advantages:

In the invention, the operation of the dual-head motor drives eccentric wheels to rotate, achieving a vibration effect. Moderate vibration can stimulate the cavernous tissue of the penis, promoting cellular metabolism and self-repair. For patients with reduced cavernous tissue function due to disease or injury, this helps improve the elasticity and toughness of the cavernous body, enhancing its blood congestion and erectile capacity. Vibration stimulation also aids in regulating and improving the nerve conduction function of the penis by prompting nerve endings to release more neurotransmitters, enhancing neural signal transmission, and making the penis more sensitive and responsive to sexual stimulation, thus facilitating better erectile function. Additionally, the vibration function introduces more variety and sensual appeal to sexual life, enriching sexual experiences, enhancing intimacy and emotional communication between partners, and exerting a positive impact on improving sexual relationships.

4. BRIEF DESCRIPTION OF ACCOMPANY DRAWINGS

1 head cover, 2 charging head, 3 pressing piece, 4 fixing piece, 5 main body, 6 flexible PCB, 7 silicone ring, 8 base, 9 right button PCB, 10 left button PCB, 11 right silicone button, 12 left silicone button, 13 sealing ring, 14 transparent mask, 15 square box, 16 support frame, 17 connecting plate, 18 connecting rod, 19 dual-head motor, 20 eccentric wheel, 21 first fixing rod, 22 spring, 23 second fixing rod, 24 water pump, 25 battery, 26 air release valve, 27 main PCB.

5. SPECIFIC EMBODIMENT OF THE INVENTION

In the following, the technical solutions in the embodiments of the present invention will be described clearly and completely with reference to the accompanying drawings in the embodiments of the present invention. Obviously, the described embodiments are only a part of the embodiments of the present invention, but not all of the embodiments. All other embodiments obtained by those of ordinary skill in the art based on the embodiments of the present invention without creative efforts shall fall within the protection scope of the present invention.

Figure 1:
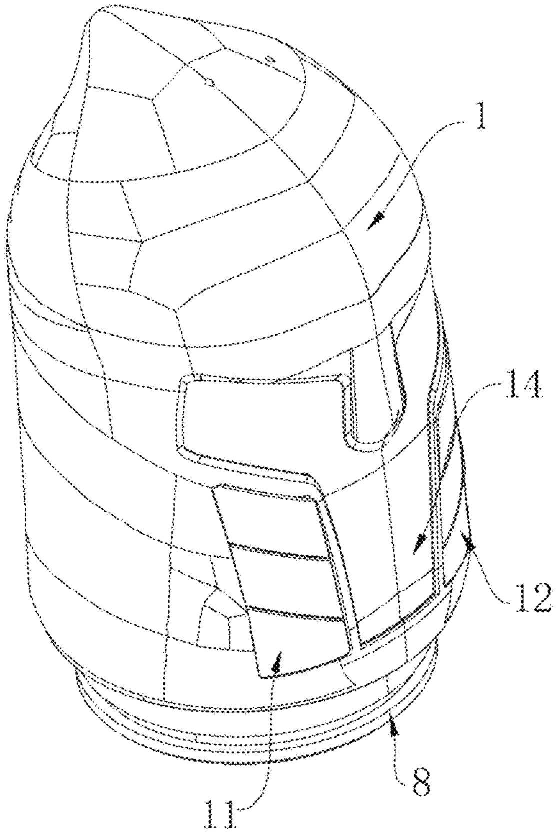
FIG. 1 is a three-dimensional schematic diagram of a penile pump proposed by the invention.
Figure 3:
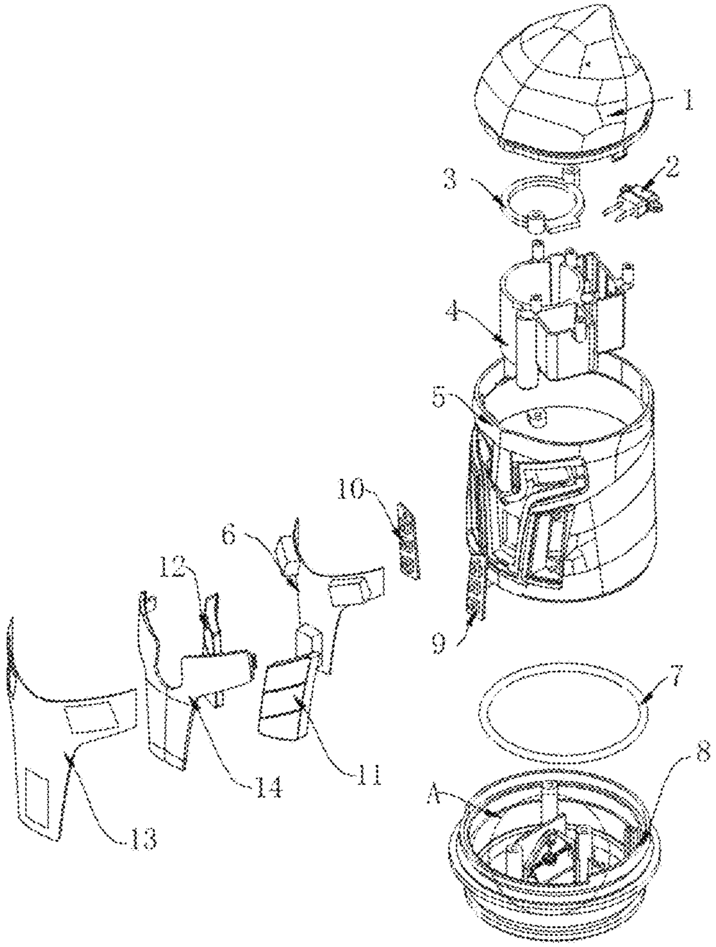
FIG. 3 is a structural schematic diagram of the fixing piece of the penile pump proposed by the invention.
Figure 4:
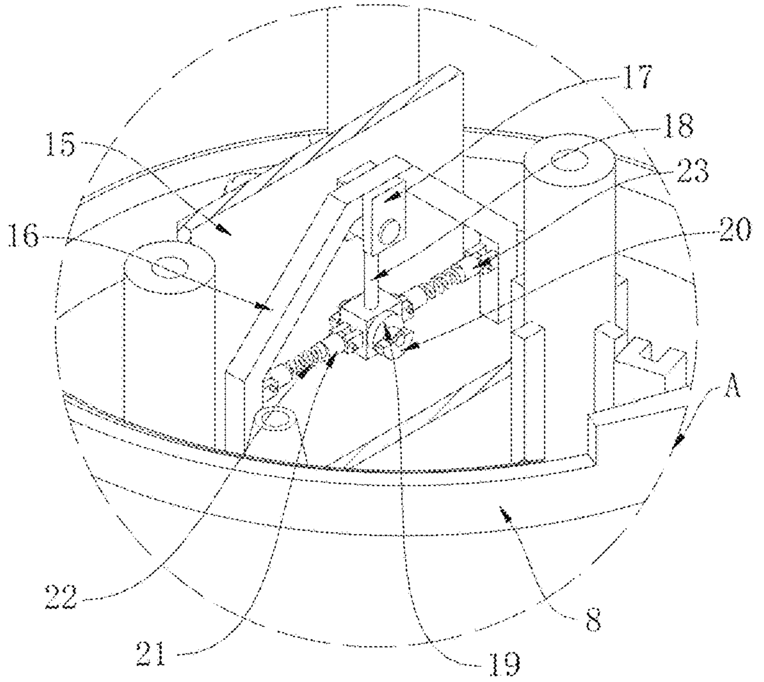
FIG. 4 is an enlarged view of section A in FIG. 3.

Referring to FIG. 1, FIG. 3, and FIG. 4, a penile pump includes a head cover 1; as a top component of the penile pump, the head cover 1 protects and encapsulates internal components of the head cover 1, which is an integral part of the overall structure of the penile pump and provides a mounting foundation for other internal components; a bottom end of the head cover 1 is fixedly connected to a main body 5; the main body 5 connects the head cover 1 and a base 8, playing a connecting role, forming the main part of the penile pump, providing installation space and protection for internal components, and also serving as the main contact area when the penile pump is held or operated; a bottom end of the main body 5 is fixedly connected to a base 8, which is located at a bottommost part of the penile pump and is fixedly connected to the main body 5, supporting the entire penile pump and maintaining the stability of the device during placement. a square box 15 is fixedly connected inside the base 8, which is fixed inside the base 8 to accommodate and protect important internal components, providing an installation framework and protective space for these components; inside the square box 15 is fixedly connected with a support frame 16, which is installed inside the square box 15 to support and fix other components such as connecting plates 17, ensuring their stable installation and operation, and serving as an important supporting component for the stability of the internal structure.

Both left and right sides of the support frame 16 are fixedly connected to connecting plates 17, which are fixed on left and right sides of the support frame 16; an interior of the connecting plate 17 is rotatably connected to a connecting rod 18, playing the role of connecting the support frame 16 and the connecting rod 18, providing a rotational installation structure for the connecting rod 18, and ensuring the stability of its movement; the interior of the connecting plate 17 is rotatably connected to the connecting rod 18, which is rotatably connected inside the connecting plate 17; a bottom end of the connecting rod 18 is fixed with a dual-head motor 19, which is used to fix the position of the dual-head motor 19 and transmit the movement of the dual-head motor 19 to the upper structure; the bottom end of the connecting rod 18 is fixed with the dual-head motor 19, and left and right driving ends are connected to eccentric wheels 20, providing power for the eccentric wheels 20 through its own rotation, which is the power source of the entire vibration component, driving the eccentric wheels 20 to rotate; two driving ends of the dual-head motor 19 are fixedly connected to eccentric wheels 20, which are fixedly connected to driving ends of the dual-head motor 19. Driven by the dual-head motor 19, they perform eccentric rotation, converting the rotational motion of the motor into the reciprocating motion of first fixing rods 21, thereby realizing the vibration function.

Both front and back sides of the eccentric wheel 20 are fixedly connected to first fixing rods 21, the eccentric wheel 20 provides stability and installation space for the first fixing rod 21; far sides of the two first fixing rods 21 are both fixedly connected to springs 22 for connecting the first fixing rods 21 and second fixing rods 23, which undergoes elastic deformation driven by the first fixing rods 21, playing the roles of buffering, shock absorption, and adjusting the vibration amplitude, while ensuring the stability of the movement of the vibration component; an adjacent side of the support frame 16 is fixedly connected to second fixing rods 23, being fixed on the adjacent side of the support frame 16 for providing a fixing point for the spring 22. The second fixing rods 23, together with the springs 22, and first fixing rods 21, form a stable structure of the vibration component, ensuring the normal realization of the vibration function; a bottom end of the head cover 1 is sleeved with a sealing component, which prevents dust and water from entering.

Figure 2:
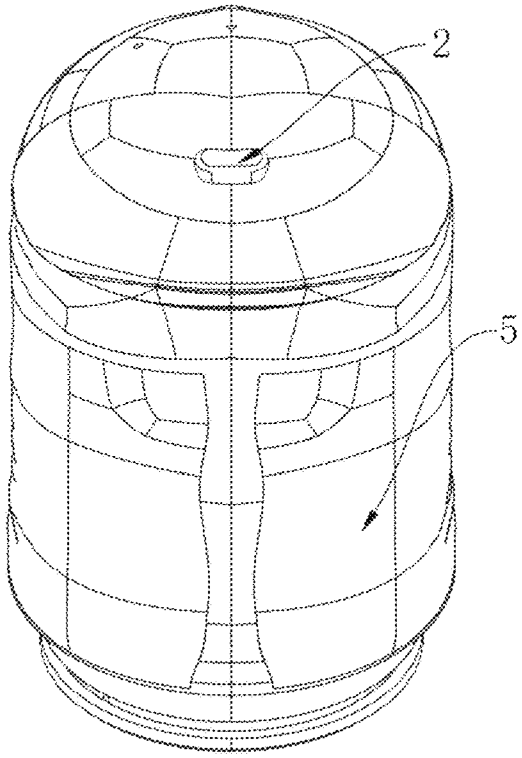
FIG. 2 is a structural schematic diagram of the main body of the penile pump proposed by the invention.
Figure 5:
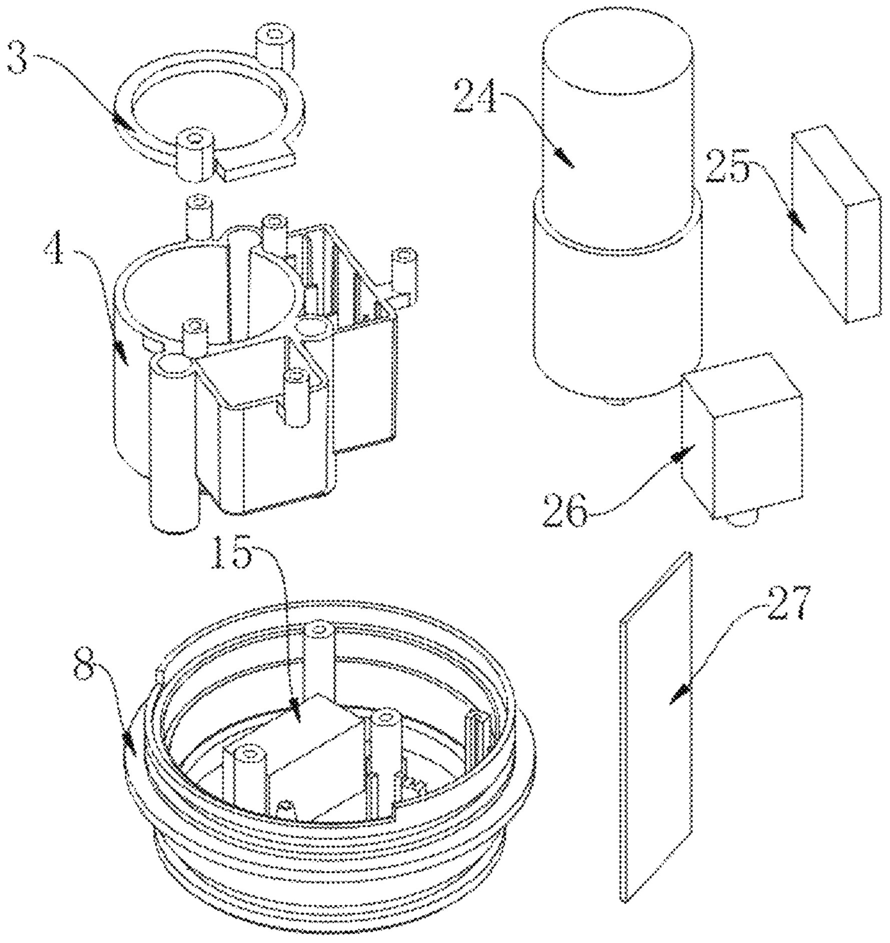
FIG. 5 is a structural schematic diagram of the base of the penile pump proposed by the invention.

Referring to FIG. 2, FIG. 3, and FIG. 5, the sealing component includes a silicone ring 7; an outer side of the silicone ring 7 is sleeved inside the main body 5; the silicone ring 7 is sleeved inside the main body 5, playing a sealing role to prevent liquid or dust from entering an inside of the main body 5. An interior of the head cover 1 is fixedly connected to a pressing piece 3; an interior of the head cover 1 is fixedly connected to a pressing piece 3; the interior of the head cover 1 is fixedly connected to the pressing piece 3 and is connected to a fixing piece 4, playing the role of fixing and pressing relevant components to ensure the stable installation of internal components. A bottom end of the pressing piece 3 is fixedly connected to the fixing piece 4, and the fixing piece 4 is connected to the pressing piece 3, providing a fixing position for components such as a water pump 24, a battery 25, and an air release valve 26, which an important supporting structure for the installation of internal components of the head cover 1. Inside a front end of the main body 5 is fixedly connected with a flexible PCB 6. The flexible PCB 6 (Flexible Printed Circuit, abbreviated as FPC) is a highly reliable and excellently flexible printed circuit board made of polyimide or polyester film as the substrate. It has the characteristics of high wiring density, light weight, thin thickness, and good bendability, and can well adapt to this product.

The flexible PCB 6 is fixed inside the front end of the main body 5, used to connect and transmit circuit signals, realizing the electrical connection between various functional components. At the same time, a front end is connected to a transparent mask 14, playing a certain role in supporting and fixing the transparent mask 14 and protecting internal components. Inside the head cover 1 is fixedly connected with a charging head 2; the charging head 2 is fixed inside the head cover 1, used to connect an external power source to charge the battery 25 of the penile pump, realizing energy supplement of the device. Inside the front end of the main body 5, on a right side is fixedly connected with a right button PCB 9; the right button PCB 9 is fixed on the right side inside the front end of the main body 5, which is a circuit carrier of a right silicone button 11, used to process the operation signals of the right silicone button 11 and transmit them to a main PCB 27; on a left side of the front end of the main body 5 is fixedly connected with a left button PCB 10; the left button PCB 10 is fixed on the left side of the front end of the main body 5, which is a circuit carrier of a left silicone button 12, used to process the operation signals of the left silicone button 12 and transmit them to the main PCB 27.

A front end of the right button PCB 9 is fixedly connected to the right silicone button 11; the right silicone button 11 is fixed at a front end of the right button PCB 9 for user operation. By pressing, it generates operation signals and transmits them to the right button PCB 9; a front end of the left button PCB 10 is fixedly connected to a left silicone button 12, the left silicone button 12 is fixed at the front end of the left button PCB 10 for user operation. By pressing, it generates operation signals and transmits them to the left button PCB 10; a front end of the main body 5 is fixedly connected to a sealing ring 13, the sealing ring 13 is fixed at the front end of the main body 5, and a flexible PCB 6 is sleeved inside, playing a sealing role to prevent external liquid, dust, etc. from entering the inside of the device. At the same time, it fixes the transparent mask 14, a front end of the sealing ring 13 is fixedly connected to the transparent mask 14, a front end of the flexible PCB 6 is fixedly connected to a back end of the transparent mask 14; the transparent mask 14 is connected to the sealing ring 13 and the flexible PCB 6, playing the role of protecting internal components and at the same time facilitating users to observe the internal situation. Inside the fixing piece 4 is fixedly connected with the water pump 24; the water pump 24 is fixed inside the fixing piece 4, used to generate negative pressure. By pumping air, a negative pressure environment is formed inside the penile pump, realizing the penile erection function.

A back end of the fixing piece 4 is fixedly connected to the battery 25, the battery 25 is fixed at the back end of the fixing piece 4, providing power for the penile pump so that the device can work normally without an external power source. On a right side of the fixing piece 4 is fixedly connected with the air release valve 26, the air release valve 26 is fixed on the right side of the fixing piece 4, used to release the negative pressure inside the penile pump, so that the device returns to the normal pressure state, facilitating post-use operation; on a right side of an interior of the base 8 is fixedly connected with a main PCB 27, the main PCB 27 is fixed on the right side of the interior of the base 8, which is the core control circuit board of the penile pump, used to receive, process, and transmit various signals, control the water pump 24, and realize various functions of the device; an outer side of the right silicone button 11 is slidably connected inside the main body 5, the main body 5 plays a role in stabilizing and guiding the right silicone button 11; an outer side of the left silicone button 12 is slidably connected inside the main body 5, the main body 5 plays a role in stabilizing and guiding the left silicone button 12. An interior of the sealing ring 13 is sleeved at the front end of the flexible PCB 6, installed at the front end of the main body 5 and sleeved at the front end of the flexible PCB 6, whose function is to form a sealing structure to prevent external impurities such as liquid and dust from entering the inside of the penile pump.

Working principle: when using this penile pump, the head cover 1, the main body 5, and the base 8 are fixedly connected in sequence to form a complete and relatively closed main structure. After the user correctly puts the penile pump on the penis, start the dual-head motor 19 located inside the base 8 and stably installed below the support frame 16 in the square box 15 through structures such as the connecting rod 18 and the connecting plate 17. Left and right driving ends of the dual-head motor 19 drive the eccentric wheels 20 to start rotating; during the rotation of the eccentric wheels 20, the first fixing rods 21 fixedly connected to front and back sides of the eccentric wheels 20 will reciprocate along with the rotation trajectory of the eccentric wheels 20. When the first fixing rods 21 move, they pull the springs 22 fixedly connected to far sides. The springs 22 generate a vibration effect during the pulling and rebounding processes. At the same time, the second fixing rods 23 cooperate with springs 22 and first fixing rods 21 to adjust and buffer the amplitude and frequency of the vibration, ensuring the stability and comfort of the vibration and avoiding damage to the penis due to excessive vibration amplitude. Inside the closed main structure, this vibration stimulation can significantly accelerate the blood circulation in the penis, help the penile corpus cavernosum to quickly become engorged with blood, and thus achieve penile erection. Moreover, during the whole process, the close connection and coordinated operation between various components enable the penile pump to assist the user to achieve the ideal penile erection effect in a safe and stable state, meeting the user's needs for penile erection function assistance.

Finally, it should be noted that the above descriptions are only preferred embodiments of the invention and are not intended to limit the invention. Although the invention has been described in detail with reference to the foregoing embodiments, those skilled in the art can still modify the technical solutions recorded in the foregoing embodiments or perform equivalent replacements for some of the technical features. Any modifications, equivalent replacements, improvements, etc. made within the spirit and principles of the invention shall be included within the protection scope of the invention.

The invention claimed is:

1. A penile pump, including a head cover and a water pump, a bottom end of the head cover is fixedly connected to a main body; a bottom end of the main body is fixedly connected to a base, a square box is fixedly connected inside the base, inside the square box is fixedly connected with a support frame, both left and right sides of the support frame are fixedly connected to connecting plates, an interior of the connecting plate is rotatably connected to a connecting rod, a bottom end of the connecting rod is fixed with a dual-head motor, and left and right driving ends of the dual-head motor are connected to eccentric wheels; both front and back sides of the eccentric wheel are fixedly connected to first fixing rods, far sides of the two first fixing rods are both fixedly connected to springs; an adjacent side of the support frame is fixedly connected to second fixing rods; a bottom end of the head cover is sleeved with a sealing component;

an interior of the head cover is fixedly connected to a pressing piece, a bottom end of the pressing piece is fixedly connected to a fixing piece, and the water pump is fixedly connected inside the fixing piece.

2. The penile pump of claim 1, wherein the sealing component includes a silicone ring; an outer side of the silicone ring is sleeved inside the main body.

3. The penile pump of claim 2, wherein inside a front end of the main body is fixedly connected with a flexible PCB.

4. The penile pump of claim 3, wherein inside the head cover is fixedly connected with a charging head; inside the front end of the main body, on a right side is fixedly connected with a right button PCB.

5. The penile pump of claim 4, wherein on a left side of the front end of the main body is fixedly connected with a left button PCB, a front end of the right button PCB is fixedly connected to a right silicone button.

6. The penile pump of claim 5, wherein a front end of the left button PCB is fixedly connected to a left silicone button, the front end of the main body is fixedly connected to a sealing ring.

7. The penile pump of claim 6, wherein a front end of the left button PCB is connected to a transparent mask, a front end of the flexible PCB is fixedly connected to a back end of the transparent mask.

8. The penile pump of claim 6, wherein an outer side of the right silicone button is slidably connected inside the main body, an outer side of the left silicone button is slidably connected inside the main body; an interior of the sealing ring is sleeved at the front end of the flexible PCB.

9. The penile pump of claim 3, wherein on a right side of the fixing piece is fixedly connected with an air release valve, on a right side of an interior of the base is fixedly connected with a main PCB.

10. The penile pump of claim 3, wherein a back end of the fixing piece is fixedly connected to a battery.

* * * * *